US007030629B1

United States Patent
Stahlmann et al.

(10) Patent No.: US 7,030,629 B1
(45) Date of Patent: Apr. 18, 2006

(54) IN LINE FLUID QUALITY SENSOR

(75) Inventors: Daniel Stahlmann, Williamsburg, VA (US); Isabelle McKenzie, Poquoson, VA (US); Ray Wildeson, Yorktown, VA (US)

(73) Assignee: Siemens VDO Automotive Corporation, Auburn Hills, MI (US)

(*) Notice: Subject to any disclaimer, the term of this patent is extended or adjusted under 35 U.S.C. 154(b) by 0 days.

(21) Appl. No.: 10/991,579

(22) Filed: Nov. 18, 2004

(51) Int. Cl.
*G01R 27/26* (2006.01)
*G01N 33/26* (2006.01)

(52) U.S. Cl. ...................... 324/663; 324/690; 73/53.05

(58) Field of Classification Search ................ 324/663, 324/658, 649, 600, 690, 691, 693, 722, 449, 324/446, 441, 439, 431, 425; 73/708, 53.01, 73/53.05, 54.16, 54.43, 861.01, 204.19; 702/99, 702/130
See application file for complete search history.

(56) References Cited

U.S. PATENT DOCUMENTS

| | | | |
|---|---|---|---|
| 4,426,616 A | 1/1984 | Maier | |
| 4,555,661 A | 11/1985 | Benson et al. | |
| 4,915,084 A | 4/1990 | Gonze | |
| 4,945,863 A | 8/1990 | Schmitz et al. | |
| 4,971,015 A | 11/1990 | Gonze | |
| 5,060,619 A | 10/1991 | Sakurai et al. | |
| 5,089,703 A | 2/1992 | Schoen et al. | |
| 5,103,184 A | 4/1992 | Kapsokavathis et al. | |
| 5,119,671 A | 6/1992 | Kopera | |
| 5,134,381 A | 7/1992 | Schmitz et al. | |
| 5,216,409 A | 6/1993 | Ament et al. | |
| 5,230,322 A | 7/1993 | Curran et al. | |
| 5,231,358 A | 7/1993 | Kapsokavathis et al. | |
| 5,255,656 A | 10/1993 | Rader et al. | |
| 5,301,542 A | 4/1994 | Meitzler et al. | |
| 5,361,035 A | 11/1994 | Meitzler et al. | |
| 5,367,264 A | 11/1994 | Brabetz | |
| 5,416,425 A | 5/1995 | Mouaici | |
| 5,435,170 A * | 7/1995 | Voelker et al. | 73/53.05 |
| 5,503,004 A | 4/1996 | Agar | |
| 5,594,163 A | 1/1997 | Suzuki | |
| 5,717,339 A | 2/1998 | Murphy et al. | |
| 5,777,210 A * | 7/1998 | Voelker et al. | 73/53.05 |
| 5,945,831 A | 8/1999 | Sargent et al. | |
| 6,781,388 B1 * | 8/2004 | Wang et al. | 324/690 |

FOREIGN PATENT DOCUMENTS

| | | |
|---|---|---|
| DE | 199 38 790 A1 | 2/2001 |
| GB | GB 2 210 459 A | 6/1989 |
| WO | WO 02/27280 | 4/2002 |

OTHER PUBLICATIONS

PCT International Search Report for PCT/US02/15931 mailed Aug. 26, 2002.
U.S. Appl. No. 6,885,199, filed May 17, 2002.
U.S. Appl. No. 6,842,017, filed Oct. 30, 2002.

(Continued)

*Primary Examiner*—Anjan Deb
*Assistant Examiner*—Hoai-An D. Nguyen

(57) ABSTRACT

A fluid quality sensor (20) includes a first electrode (24) that has a fluid passageway (22) that is adapted to be placed in line with at least one fluid conduit (30). A housing (40) is supported on the first electrode (24) in one example by overmolding a portion (48) of the housing onto a portion of the first electrode (24). A second electrode (50) is supported within the fluid passageway (22) and electrically isolated from the first electrode (24). The first electrode (24) and the second electrode (50) operate as a capacitor for making fluid quality determinations.

25 Claims, 3 Drawing Sheets

OTHER PUBLICATIONS

U.S. Appl. No. 6,927,583, filed Jun. 2, 2003.
U.S. Appl. No. 10/991,245, filed Nov. 17, 2004.
U.S. Appl. No. 11/071,820, filed Mar. 3, 2005.
U.S. Appl. No. 11,071,853, filed Mar. 3, 2005.

* cited by examiner 20
28
46
44
60
56
52'
48
54
42
50'
40
24
22
26

IN LINE FLUID QUALITY SENSOR

FIELD OF THE INVENTION

This invention generally relates to a sensor for determining a fluid quality. More particularly, this invention relates to a sensor that can be placed in line along a fluid flow path for determining a quality of a fluid flowing along the path.

DESCRIPTION OF THE RELATED ART

Various fluid quality sensors are known. One type of determination made by such sensors is the concentration of one or more components within a fluid mixture. Some example sensors use a capacitor-based measurement technique to make a determination regarding the quality of interest.

One example situation is in automotive fuel systems. It is useful, for example, to determine the alcohol content within a fuel mixture for purposes of adjusting fuel supply parameters in fuel injection systems. A known sensor for making such a determination is shown in U.S. Pat. No. 5,367,264. That document discloses a way of determining the alcohol content of a fuel mixture based on a capacitance and conductance of a capacitor-based measuring circuit, which is exposed to the fuel mixture. A variety of such devices are known.

Another situation where a fluid quality determination is useful is in a catalytic converter arrangement that uses a known selective catalytic reaction to control vehicle engine emissions. In this situation, it is useful to determine a urea concentration level in a fluid supply to the catalytic converter. Such devices utilize a mixture of urea and de-ionized water for producing ammonia hydroxide, which is used to control the nitrogen oxide in exhaust emissions. It is desirable to be able to provide an indication of a urea concentration level so that the catalytic converter will perform as needed or desired.

One shortcoming of previously proposed devices is that they are typically limited to very specific applications. Another limitation is that the placement of such devices is commonly limited to a supply or reservoir tank. There is a need for a more versatile arrangement that can accommodate various situations and that can be more readily incorporated into an appropriate system. This invention addresses those needs.

SUMMARY OF THE INVENTION

An example disclosed embodiment of a sensor device for detecting a fluid property includes a first electrode having a fluid passageway extending between ends of the first electrode. At least one of the ends is adapted to be coupled to a fluid conduit. A second electrode is supported within the first electrode fluid passageway and electrically isolated from the first electrode. Fluid in the fluid passageway can fill a space between the first and second electrodes. A housing is supported on the first electrode for housing electronics used to make a determination regarding the fluid property. In one example, the housing is overmolded onto the first electrode.

The example sensor device can be inserted into a fluid supply line, for example. By having the sensor positioned in-line with an appropriate fluid passageway, the sensor is able to provide fluid quality information regarding substantially all of the fluid passing through the passageway. This is an advantage compared to arrangements where a sensor is only exposed to fluid within a limited portion of a supply tank, for example. Additionally, the disclosed sensor arrangement can be readily accommodated into a variety of arrangements and does not require modification of a supply tank, for example.

The various features and advantages of this invention will become apparent to those skilled in the art from the following detailed description of the currently preferred embodiments. The drawings that accompany the detailed description can be briefly described as follows.

DETAILED DESCRIPTION OF THE PREFERRED EMBODIMENT

Figure 1:
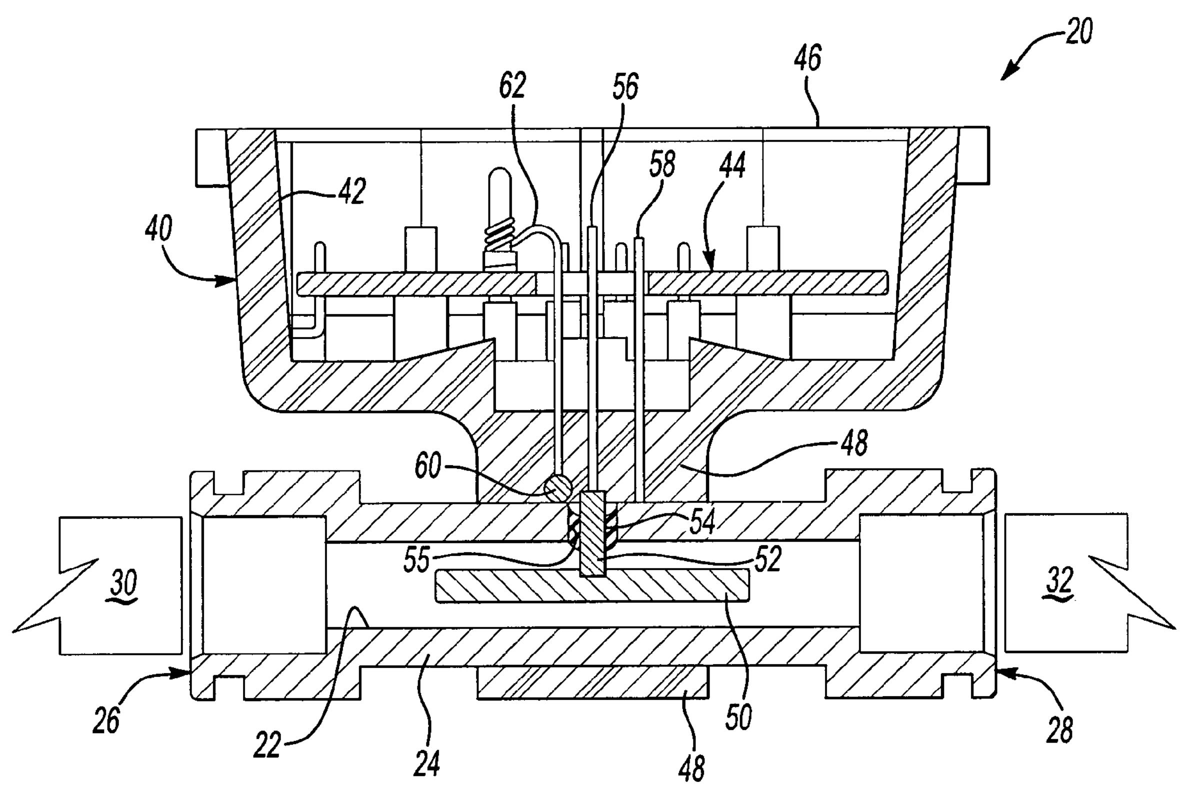
FIG. 1 is a cross-sectional illustration showing an example embodiment of a sensor designed according to this invention.

As can be appreciated from FIG. 1, a fluid quality sensor device 20 has a fluid passageway 22 through which a fluid of interest can flow. The fluid passageway 22 is formed through a first electrode 24. A first end 26 and a second end 28 of the first electrode 24 are adapted to be coupled with at least one fluid conduit 30. In the illustrated example, the first end 26 can be coupled with a first conduit 30 and the second end 28 can be coupled with a second conduit 32. In one example, the conduits 30 and 32 are sections of the same conduit.

By coupling the first electrode 24 with the conduits 30 and 32, the fluid passageway 22 accommodates fluid flowing through the conduits 30 and 32 and is in line with the conduits of an appropriate portion of a fluid handling system. In one example, the conduits 30 and 32 are fuel supply lines. In another example, the conduits 30 and 32 are a urea mixture supply for a catalytic converter arrangement.

The sensor device 20 includes a housing portion 40 that is supported on the first electrode 24. In the illustrated example, a container portion 42 supports electronics on a printed circuit board 44. A cover 46 closes off the container portion 42 to protect the electronics on the circuit board 44 from contamination, for example. A support portion 48 is coupled with the container portion 42 and received about at least a portion of the exterior of the first electrode 24.

In the illustrated example, the support portion 48 is overmolded onto the first electrode 24. The entire housing 40 in the illustrated example is molded at one time and secured into position onto the first electrode 24 during the molding process.

Figure 3:
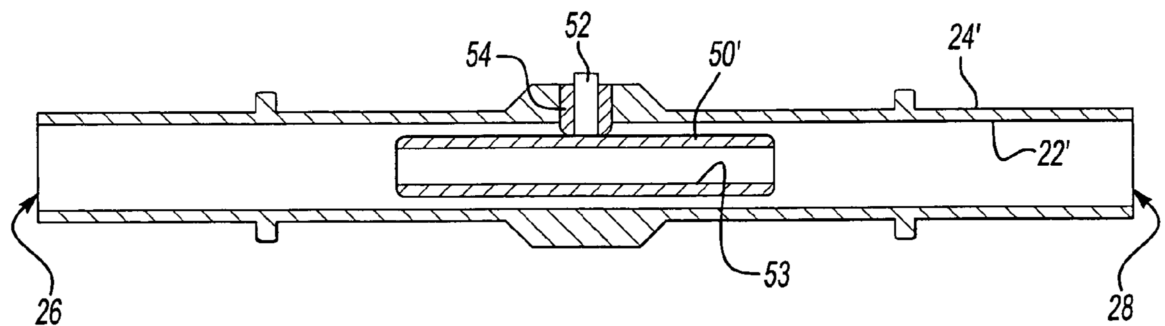
FIG. 3 is a cross-sectional illustration showing selected portions of an alternative embodiment of a sensor designed according to this invention.

A second electrode 50 is supported within the fluid passageway 22 such that fluid flowing through the passageway 22 fills spacing between the inside of the first electrode 24 and the exterior of the second electrode 50. In the example of FIG. 1, the second electrode 50 comprises a solid rod. In the example of FIG. 3, the second electrode 50' comprises a hollow tube. In the example of FIG. 3, the second electrode 50' includes a second fluid passageway 53 through which the fluid flowing in the passageway 22' may flow.

The example of FIG. 1 is useful in situations where the fluid of interest has a relatively high conductivity such as a urea concentration fluid sensor, for example. The example of FIG. 3 is useful in situations including a fluid of lower conductivity such as an automotive fuel alcohol concentration sensor, for example. Given this description, those skilled in the art will be able to select appropriate configurations of the second electrode and size it according to a size of the first electrode to meet the needs of their particular situation.

The first electrode 24 and the second electrode 50 operate as a cathode and an anode of a capacitor, respectively. Capacitor-based fluid quality or property measurement techniques are known.

As best appreciated from FIG. 1, the second electrode 50 is supported within the fluid passageway 22 by a mounting member 52 that has a first end secured to the second electrode 50 and another portion supported by the first electrode 24. In one example, one end of the mounting member 52 is brazed to the second electrode 50. An insulator 54 electrically isolates the mounting member from the first electrode 24 and, therefore, the second electrode 50 remains electrically isolated from the first electrode 24. In the event that fluid fills the passageway 22, the fluid between the first electrode 24 and the second electrode 50 builds a dielectric for capacitor-based fluid quality measurements.

In the example of FIG. 1, the mounting member 52 comprises a pin and the insulator 54 comprises a glass seal, which serves the dual function of supporting the mounting member 52 in an electrically isolated manner from the first electrode 24 and providing a fluid-tight seal of an opening 55 in the first electrode 24 through which the mounting member 52 is partially received.

An electrically conductive member 56 is coupled with the mounting member 52 and appropriate portions of the electronics on the printed circuit board 44 (see FIG. 2) for selectively powering the second electrode 50. Another electrical conductor 58 is coupled with the first electrode 24 and appropriate electronics on the printed circuit board 44. By operating the capacitor comprising the first electrode 24 and second electrode 50 in a desired manner, the fluid quality of interest can be determined. In one example, the sensor electronics use known techniques for making such a determination.

Another feature of the embodiment of FIG. 1 is a temperature sensor 60 supported by the housing 40. In this example, the temperature sensor 60 comprises a known NTC device and is supported by the support portion 48 of the housing 40 such that the temperature sensor device 60 is in contact with an exterior surface on the first electrode 24. Electrical conductors 62 couple the temperature sensor device 60 to appropriate electronics supported on the printed circuit board 44 for operating the device in a known manner. The temperature information can be used as known for making fluid quality determinations.

A significant advantage of the example arrangements is that the sensor 20 can be readily incorporated into a fluid supply arrangement and made part of a fuel supply line, for example. In one example, one end of the first electrode 24 is secured to a tank or reservoir while the other end is secured to a conduit that allows fluid to flow into or out of the tank or reservoir.

Figure 2:
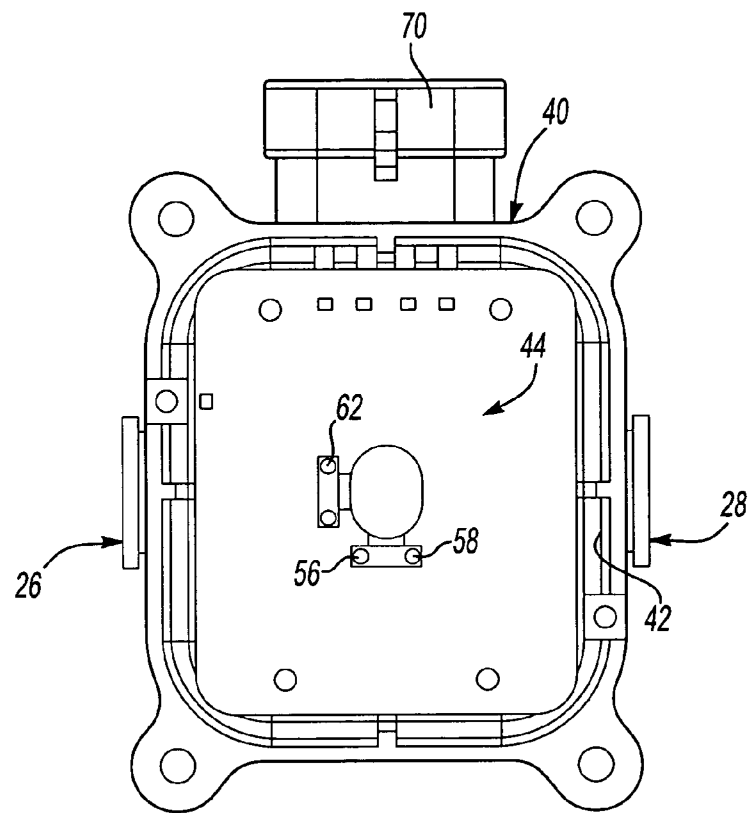
FIG. 2 is an elevational view seen from the top of the illustration of FIG. 1.

As can be appreciated from FIG. 2, the example housing 40 includes an electrical connector portion 70 that allows for connecting the electronics supported by the printed circuit board 44 with other devices. In one example, the printed circuit board 44 supports a controller such as a microprocessor and a plurality of oscillators for operating the capacitor, which comprises the first electrode 24 and the second electrode 50, in a known manner for making measurements such as capacitance, permittivity, conductivity or a combination of these. Known techniques for making such measurements are used in one example.

Figure 4:
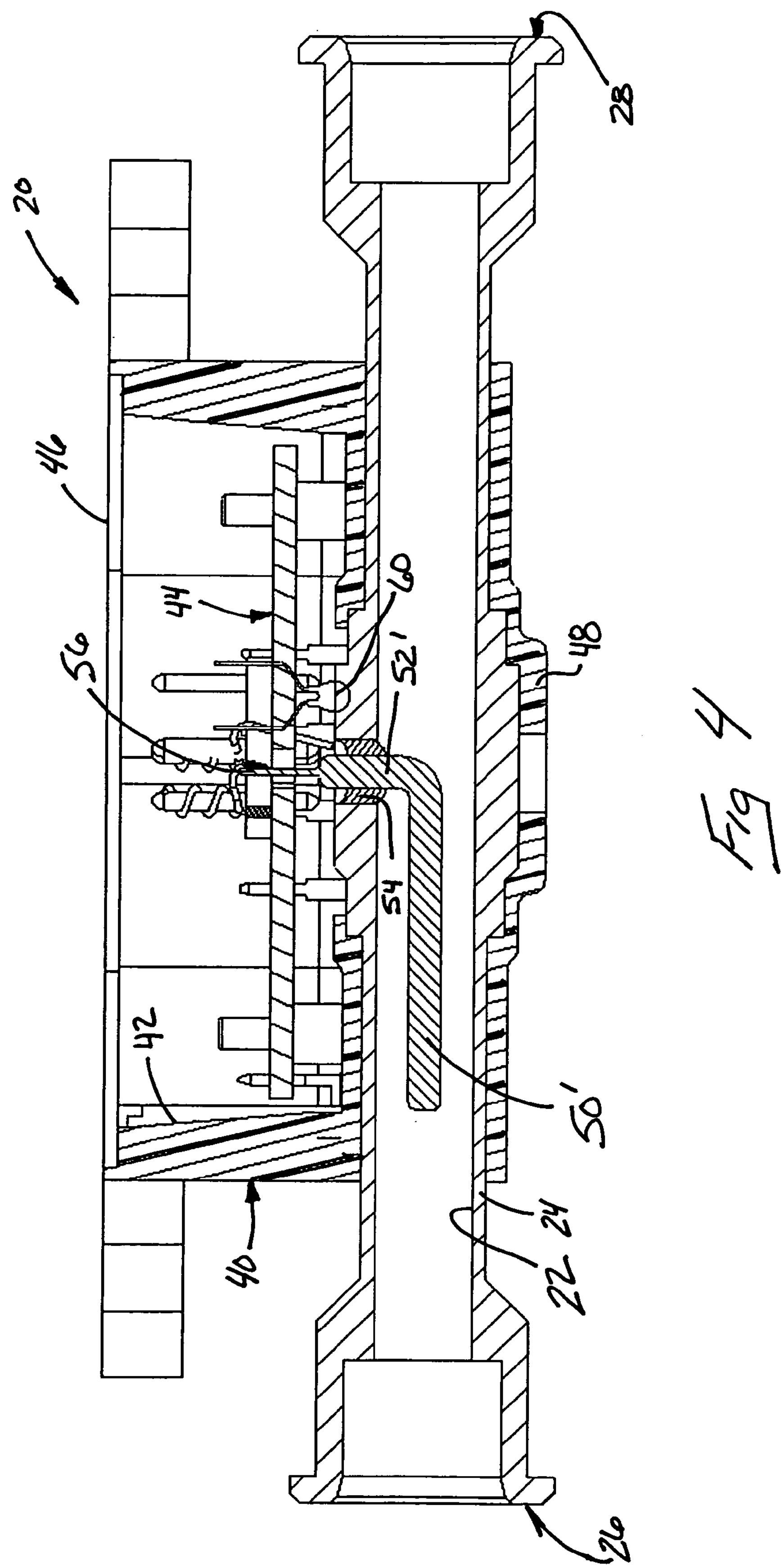
FIG. 4 shows another example embodiment.

The example of FIG. 4 includes a modified second electrode 50' that is shaped to avoid a separate mounting member. Instead, a portion 52' is bent in a direction to facilitate mounting the second electrode 50' within a corresponding passageway 22. The housing portion 40' is also modified compared to the embodiment of FIG. 1 as can be appreciated from the drawing.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A sensor device for detecting a fluid property, comprising:

a first electrode having a fluid passageway extending between ends of the first electrode, at least one of the ends being adapted to be coupled to a fluid conduit;

a second electrode supported within the first electrode fluid passageway and electrically isolated from the first electrode such that fluid in the passageway can fill a space between the first and second electrodes;

a housing supported at least partially on the first electrode and electrical conductors that are coupled with the electrodes supported at least partially by the housing; and an electrically conductive mounting member secured to the second electrode and having a portion supported by the first electrode.

2. The device of claim 1, wherein the housing is overmolded onto a portion of the first electrode.

3. The device of claim 1, wherein the first electrode comprises a cylindrical portion defining the fluid passageway and the second electrode comprises a parallel cylindrical portion parallel to the fluid passageway and a transverse portion that is transverse to the parallel portion.

4. The device of claim 1, wherein the second electrode comprises a solid rod.

5. The device of claim 1, wherein the second electrode comprises a hollow tube.

6. The device of claim 3, wherein the transverse portion is received at least partially through the first electrode.

7. The device of claim 1, including an insulator electrically isolating the mounting member from the first electrode.

8. The device of claim 7, wherein the insulator comprises a glass seal.

9. The device of claim 1, wherein the mounting member comprises a pin having one end connected to the second electrode and a second end supported by the first electrode.

10. The device of claim 9, wherein the first electrode has an opening, the pin second end is at least partially received in the opening and including a glass seal surrounding the part of the pin received in the opening and closing off the opening in a fluid-tight manner.

11. The device of claim 1, wherein the first electrode comprises a cathode and the second electrode comprises an anode of a capacitor.

12. The device of claim 1, including a temperature sensor supported by the housing, the temperature sensor being in contact with the first electrode for sensing a temperature of fluid in the fluid passageway.

13. The device of claim 1, wherein the first electrode comprises a tube having connection portions at ends of the tube that are adapted to establish a fluid-tight, sealed connection with a fluid conduit.

14. The device of claim 6, including a glass seal between the transverse portion and the first electrode.

15. A fluid supply system, comprising:

a conduit for directing a flow of fluid;

a sensor in line with the conduit having a first electrode directly coupled to the conduit and a second electrode supported within the first electrode such that fluid flowing in the conduit fills a space between the first and second electrodes; and a housing supported at least partially on the first electrode and electrical conductors that are coupled with the electrodes supported at least partially by the housing.

16. The system of claim 15, wherein the first electrode comprises a cylindrical portion defining a fluid passageway through the first electrode and the second electrode comprises a parallel cylindrical portion parallel with the fluid passageway and a transverse portion that is transverse to the parallel portion.

17. The system of claim 15, wherein the second electrode comprises a solid rod.

18. The system of claim 15, including a mounting member secured to the second electrode and an insulator electrically insulating the mounting member from the first electrode.

19. The system of claim 15, wherein the housing is overmolded onto a portion of the first electrode.

20. The system of claim 18, wherein the mounting member is electrically conductive.

21. A sensor device for detecting a fluid property, comprising:

a first electrode having a fluid passageway extending between ends of the first electrode, at least one of the ends being adapted to be coupled to a fluid conduit;

a second electrode comprising a solid rod and supported within the first electrode fluid passageway and electrically isolated from the first electrode such that fluid in the passageway can fill a space between the first and second electrodes; and a housing supported at least partially on the first electrode and electrical conductors that are coupled with the electrodes supported at least partially by the housing.

22. A sensor device for detecting a fluid property, comprising:

a first electrode having a fluid passageway extending between ends of the first electrode, at least one of the ends being adapted to be coupled to a fluid conduit;

a second electrode supported within the first electrode fluid passageway and electrically isolated from the first electrode such that fluid in the passageway can fill a space between the first and second electrodes;

a housing supported at least partially on the first electrode and electrical conductors that are coupled with the electrodes supported at least partially by the housing; and a mounting member comprising a pin having one end connected to the second electrode and a second end supported by the first electrode.

23. The device of claim 22, wherein the first electrode has an opening, the pin second end is at least partially received in the opening and including a glass seal surrounding the part of the pin received in the opening and closing off the opening in a fluid-tight manner.

24. A sensor device for detecting a fluid property, comprising:

a first electrode having a fluid passageway extending between ends of the first electrode, at least one of the ends being adapted to be coupled to a fluid conduit;

a second electrode supported within the first electrode fluid passageway and electrically isolated from the first electrode such that fluid in the passageway can fill a space between the first and second electrodes, the second electrode having a parallel portion aligned generally parallel with the first electrode fluid passageway and a transverse portion that is transverse to the parallel portion; and a housing supported at least partially on the first electrode and electrical conductors that are coupled with the electrodes supported at least partially by the housing.

25. The device of claim 24, wherein the transverse portion is at least partially received through the first electrode for supporting the second electrode relative to the first electrode.

* * * * *